(12) United States Patent  
Varley (10) Patent No.: US 7,833,568 B2
(45) Date of Patent: Nov. 16, 2010

(54) METHOD OF DETERMINING THE CUTICLE SCALE HEIGHT OF FIBERS

(75) Inventor: Adam R. Varley, New York, NY (US)

(73) Assignee: Vartest Labs Inc., New York, NY (US)

( * ) Notice: Subject to any disclaimer, the term of this patent is extended or adjusted under 35 U.S.C. 154(b) by 811 days.

(21) Appl. No.: 11/794,655

(22) PCT Filed: Jan. 23, 2006

(86) PCT No.: PCT/US2006/002657

§ 371 (c)(1),
(2), (4) Date: Jun. 27, 2007

(87) PCT Pub. No.: WO2006/083650

PCT Pub. Date: Aug. 10, 2006

(65) Prior Publication Data

US 2010/0032563 A1    Feb. 11, 2010

(51) Int. Cl.
*B05D 3/02*    (2006.01)
(52) U.S. Cl. .......................................... 427/8; 250/307
(58) Field of Classification Search ................. 250/307; 427/8

See application file for complete search history.

(56) References Cited

U.S. PATENT DOCUMENTS 4,144,027 A    3/1979    Habib
4,319,879 A    3/1982    Hojo et al.
4,396,388 A    8/1983    Hojo et al.
5,298,320 A    3/1994    Geoffrey
5,385,580 A *  1/1995    Schmitt ..................... 623/1.52
5,487,858 A *  1/1996    Schmitt ..................... 264/103
5,496,364 A *  3/1996    Schmitt ..................... 623/1.52
2005/0238793 A1  10/2005  Sherman et al.
2008/0034801 A1*  2/2008  Canham et al. ............... 65/439
2010/0165282 A1*  7/2010  Mochizuki et al. .......... 349/155

OTHER PUBLICATIONS

Dobb et al., "Morphology of the Cuticle Layer in Wool Fibres and Other Animal Hairs," Journal of the Textile Institute, Apr. 1961.
Marshall et al., "Possible Identification of Specialty Fibers by Electrophoresis," Textile Research Journal, http://trj.sagepub.com, 1984; 54; 126.
"Quantitative Analysis of Blends of Wool with Specialty Fibres by Scanning Electron Microscopy," published by The Woolmark Company, new draft tm-58, Wednesday, Jul. 8, 1998.
Wortmann et al., "Quantitative Fiber Mixture Analysis by Scanning Electron Microscopy," Textile Research Journal, Jul. 1986, pp. 442-446.
Leeder et al., "Properties and Performance of Goat Fibre," RIRDC Publication No. 98/22, RIRDC Project No. ULA-8A, Mar. 1998.
Robson, D., "Animal Fiber Analysis Using Imaging Techniques: Part II," Textile Research Journal 2000; 70; 116, http://trj.sagepub.com.

* cited by examiner

*Primary Examiner*—Nikita Wells
*Assistant Examiner*—Johnnie L Smith
(74) *Attorney, Agent, or Firm*—Abelman, Frayne & Schwab (57) ABSTRACT

Accurate and reproducible measurements of the cuticle scale height of naturally occurring proteinaceous fibers can be made by measuring the scale height of the fiber while it is vertically oriented beneath a scanning electron microscope.

4 Claims, 9 Drawing Sheets

METHOD OF DETERMINING THE CUTICLE SCALE HEIGHT OF FIBERS

BACKGROUND OF THE INVENTION

1. Field of the Invention

The present invention relates to a method for measuring the cuticle scale height of fibers and, more particularly, to an objective and reliable method for the measurement of the cuticle scale height of naturally occurring, proteinaceous fibers employing a scanning electron microscope (SEM).

2. Description of the Prior Art

About 16,000 tons of raw cashmere are produced globally each year. Approximately 50% of raw cashmere is lost to scouring and dehairing, meaning that global production of cashmere for use in garments is about 8000 tons or 16,000,000 pounds. The United States definition of cashmere for testing by The American Association of Textile Chemists and Colorists (AATCC) was broadened in 2001 by increasing the average diameter for cashmere from 15-16 microns to 15-18.5 microns average, meaning that a wider range of specialty animal fibers, such as yak, could more readily be substituted for cashmere with a lessened expectation of detection.

Recent prices for dehaired dark Afghan cashmere are $41 per kilo whereas dehaired medium yak hair is $15 per kilo. Even greater differences in price exist between white Chinese cashmere at $69 per kilo and 17 micron wool at $8.83/kilo. Numerous articles in the literature, court cases, and the continuing search for new analytical technologies have all pointed to the need for increased accuracy and objectivity in the quantitative analysis of intimate blends of cashmere with wool.

Several different types of technology have been brought to bear on the problem of accurate repeatable objective blend analysis of cashmere blends, a sign in itself that the problem is an important one that merits research effort to determine a better test method. This need is consistent with society's broader demand over time for standardized measurement techniques in commerce [1]. DNA probes, electrophoresis of extracted amino acids, high pressure liquid chromatography of treated fibers, Fourier transform infra-red analysis both with and without neural nets as well as image analysis both with and without neural nets have all been applied to the problem of increasing the accuracy of cashmere intimate blend analysis [2, 3, 4, 5, 6, 7, 8, 9]. Notwithstanding these efforts, published research indicates that both scanning electron microscope based testing and, indeed, all other applied technologies to date, including both transmitted light microscopy and scanning electron microscopy, are deficient in their ability to consistently and objectively differentiate between cashmere and other animal fibers [7].

Cuticle scale height measurement for the objective determination of blend type has been claimed to be able to categorically and without exception differentiate objectively between wool and all specialty animal fibers [8]. International Wool Textile Organization Test. Method (IWTO) 58 embodies the work performed by various researchers on quantitative blend analysis using SEM, particularly The German Wool Research Association. While IWTO 58—displays large amounts of data on cuticle scale height, it gives no specific instructions on exactly where, how, or how many scales should be measured in order to derive scale height [9].

The scale heights of fibers in IWTO 58 and all other documents concerning scale height to date are obtained by measuring the scales while the fibers snippets are lying down longitudinally. Early animal textile fiber researchers [10] realized the limitations of this method in that profile artifacts and limited scale views are often presented for measurement and uninterrupted sequential scale height measurement is prevented.

Using the traditional method, scale height measurements are taken by focusing on a scale edge at 10000× or higher while the fiber snippet is lying longitudinally on an SEM stub. After this scale is measured another measurable scale edge may be sought after, although no sample size number of scales to be measured is given. The SEM operator then hunts along the fiber surface until he or she subjectively judges that an appropriate scale has presented itself for measurement. This process interjects an unavoidable element of the personal equation into the process of cuticle scale height measurement which may, in part, be responsible for the difficulty experienced in the consistent use of this technique.

SUMMARY OF THE INVENTION

It has now been found that accurate and objective cuticle scale height measurements of naturally occurring proteinaceous fibers can be obtained with the use of a scanning electron microscope, provided the fibers are oriented and mounted vertically and scanned when mounted in such vertical orientation.

As will be apparent henceforth, vertically mounted fibers provide the microscopist with a clear and unambiguous scale height for each cuticle scale, which heretofore was unavailable when measured by conventional longitudinal mounting and scanning methods.

DETAILED DESCRIPTION OF THE INVENTION

The present invention provides an accurate and objective method for determining the cuticle scale height of a naturally occurring, proteinaceous fiber, which comprises:

a) selecting a naturally-occurring, proteinaceous fiber for cuticle scale height determination;

b) mounting said fiber substantially vertically for imaging by a scanning electron microscope;

c) imaging said fiber under said scanning electron microscope under sufficient magnification to discern the scale height of a vertically oriented cuticle; and d) taking at least one reading of the height of the cuticle along at least one scale of said fiber.

Figure 1:
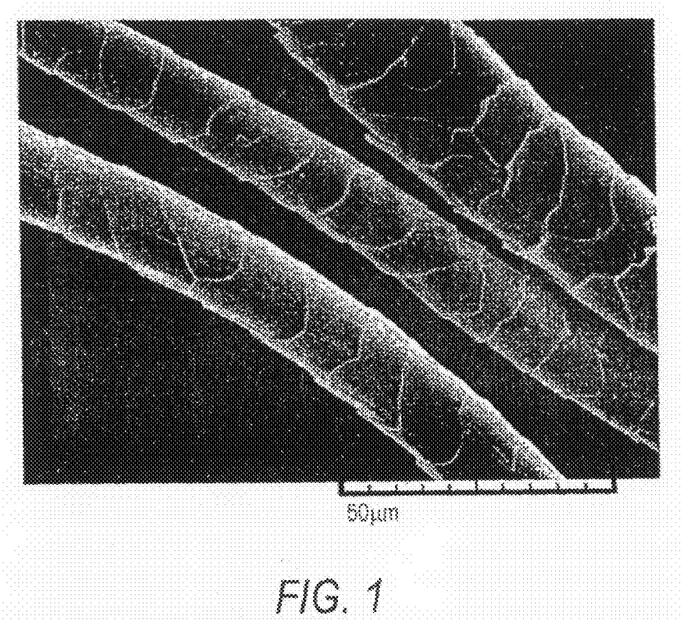
FIG. 1 is a photomicrograph of a fiber which has been mounted longitudinally and scanned longitudinally by a SEM (Scanning Electron Microscope) employing the measurement technique of the prior art at a magnification of 1370×.
Figure 2:
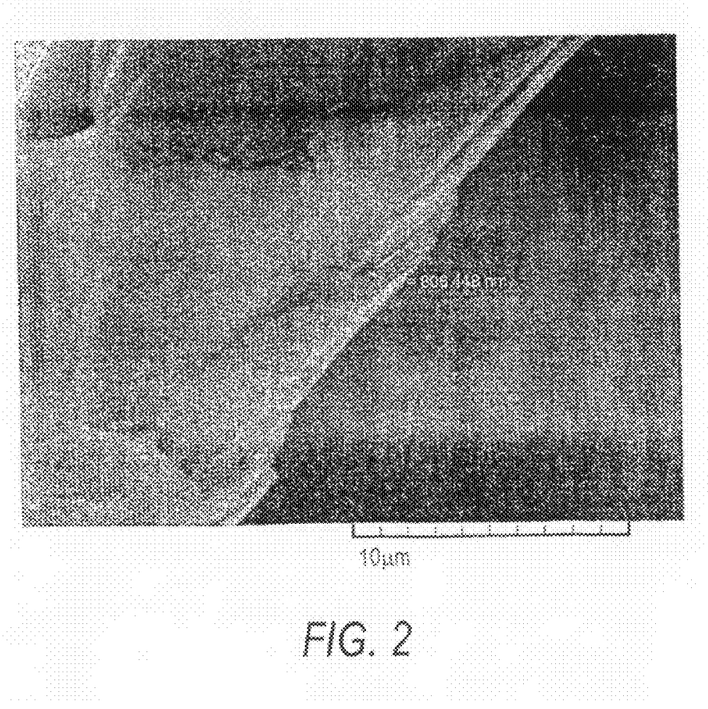
FIG. 2 is the same fiber as in FIG. 1 which has been subjected to the longitudinal-type scanning of the prior art at a magnification of 7750×.

It can be readily seen from an examination of FIGS. 1 and 2 that by employing the longitudinal scanning of a fiber shaft in accordance with the prior art, only a few scales are visible at a time, and the cuticle scale height of the fiber shaft can only be measured with difficulty.

It becomes readily evident from an examination of FIGS. 8-16, which employ the method of the present invention, namely, the vertical mounting of the fibers, that there is an increase in the number of scales which are visible, which, in turn, allows the microscopist to make the necessary measurements in sequence with a high level of confidence and reduces the level of subjectivity that is inherent with longitudinal analysis. By the use of the sequential vertical method of the present invention, the microscopist is locked into working with a group of contiguous scales. No subjective hunting for additional scale specimens is required; once the first scale is measured the other fibers are obtained, such that the microscopist has no personal choice with respect to the subsequent scales which are measured.

Figure 3:
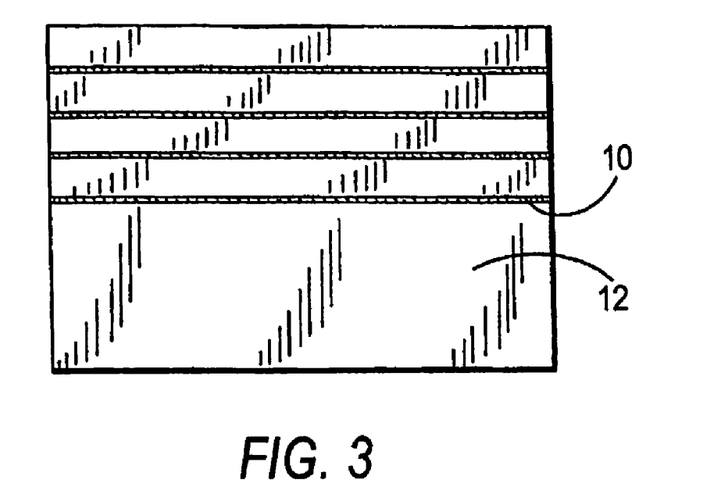
FIG. 3 depicts four (4) proteinaceous, naturally occurring animal fibers mounted on a copper tape in accordance with the present invention.

The first step in the microscopy process, as can be seen in FIG. 3, involves selecting a plurality of animal fibers 10 which are then mounted on a conductive copper tape 12. Each of the mounted fibers are laid parallel to one another and are spaced from each other the same distance, when measured in the length direction.

Figure 4:
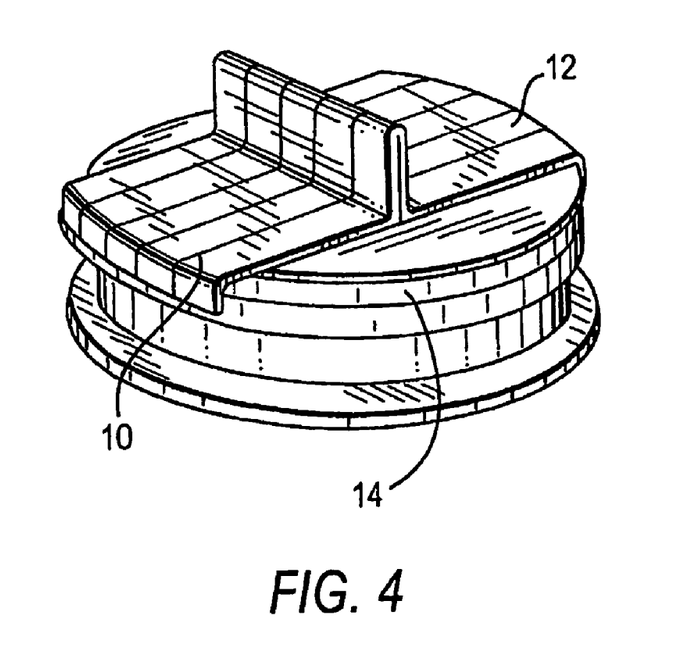
FIG. 4 depicts vertically oriented fibers in accordance with the present invention mounted on copper tape, as shown in FIG. 3, and then mounted vertically on the stub of an SEM.

Turning now to FIG. 4, the copper tape 12 bearing the fibers 10 is transferred and mounted onto an SEM stub 14 made of aluminum, and the tape 12 is bent in the middle thereof to create a substantially 90° angle with respect to the base of stub 14. The bent portion of the copper tape rises from about ⅛" to ¼" above the surface of stub 14. The copper tape 12 and fibers 10 mounted thereon are then coated with gold by a Cressington 108 sputter coater or a similar device. A 12 mm diameter double-sided adhesive carbon conductive tab is affixed to the aluminum mounting surface.

Figure 5:
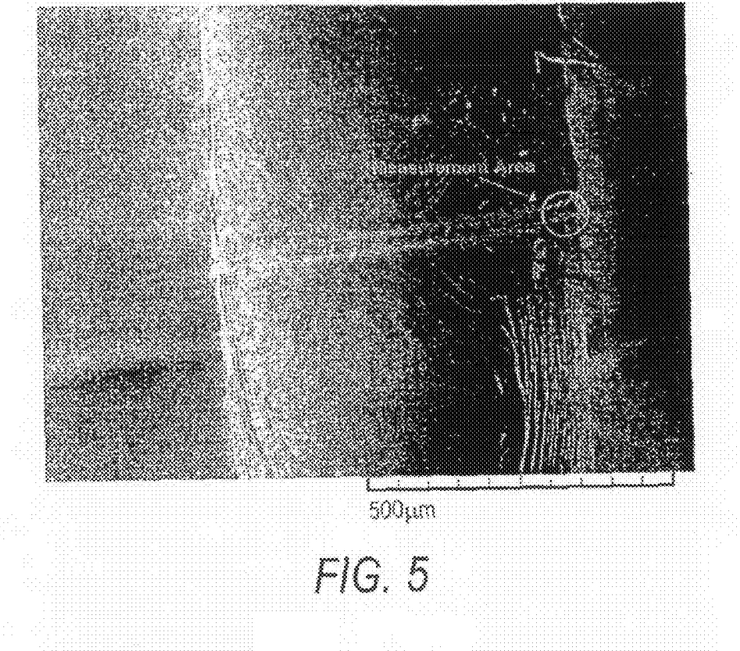
FIG. 5 depicts a vertical scale height measurement at an SEM magnification of 223× in accordance with the present invention.

FIG. 5 shows the measurement area of a naturally occurring proteinaceous animal fiber which is bent over a copper tape for measurement along its vertical extent in accordance with the present invention.

Figure 6:
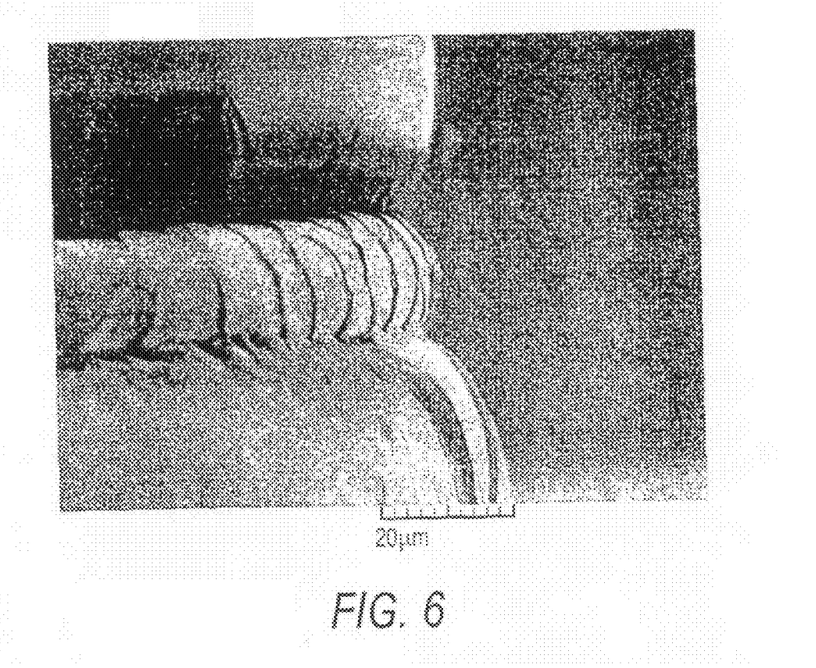
FIG. 6 shows the cuticle scale heights of the fibers of FIG. 5 presenting themselves in sequence for measurement on an SEM at a magnification of 2460×.

FIG. 6, which is the same fiber as in FIG. 5 at about 10× the magnification, shows the same fiber with several scale edges now visible and presenting themselves in sequence for measurement.

Figure 7:
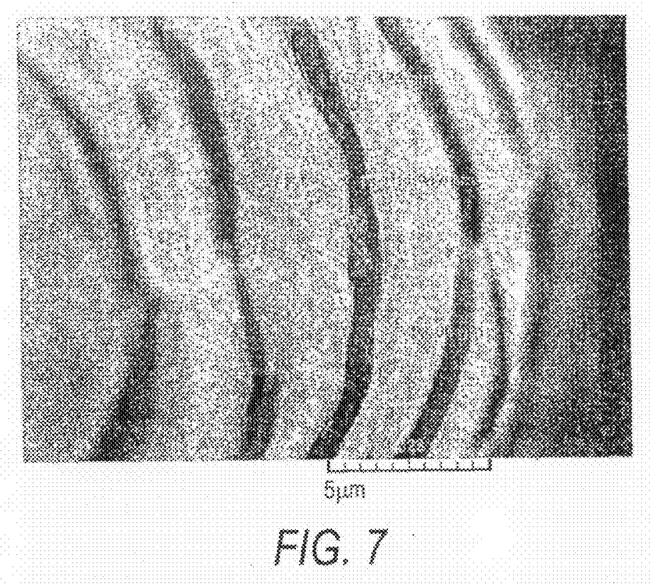
FIG. 7 shows a single scale edge of FIG. 6 for measurement at a magnification of 12,930×.

FIG. 7, which is the same fiber as seen in FIG. 6 at about 5× the magnification, illustrates four scale measurements which were made along a single scale edge by employing the method of the present invention, namely, vertical orientation of the fiber during scanning and sequential measurements.

Figure 8:
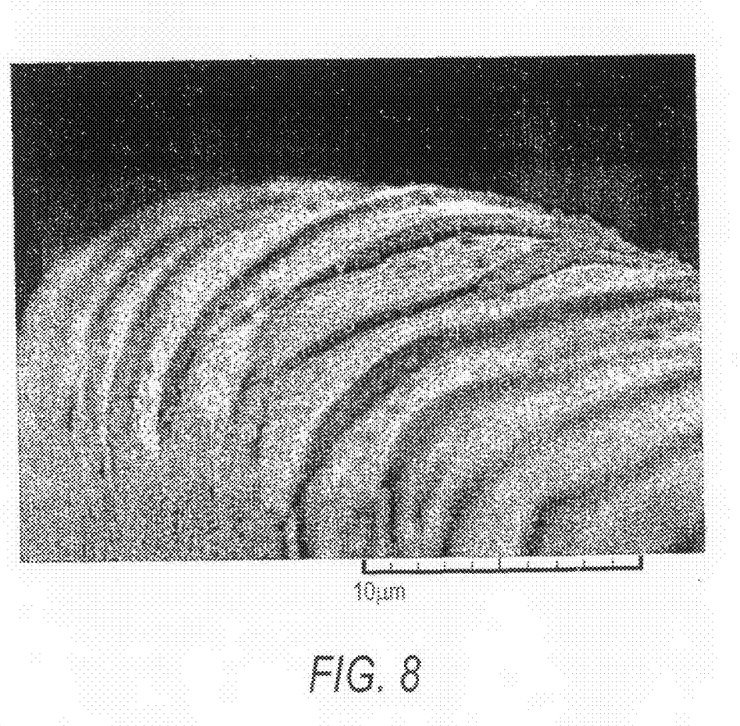
FIG. 8 is an SEM image of a cashmere fiber with an NIST internal standard and a scale sequence at a magnification of 6490×.
Figure 9:
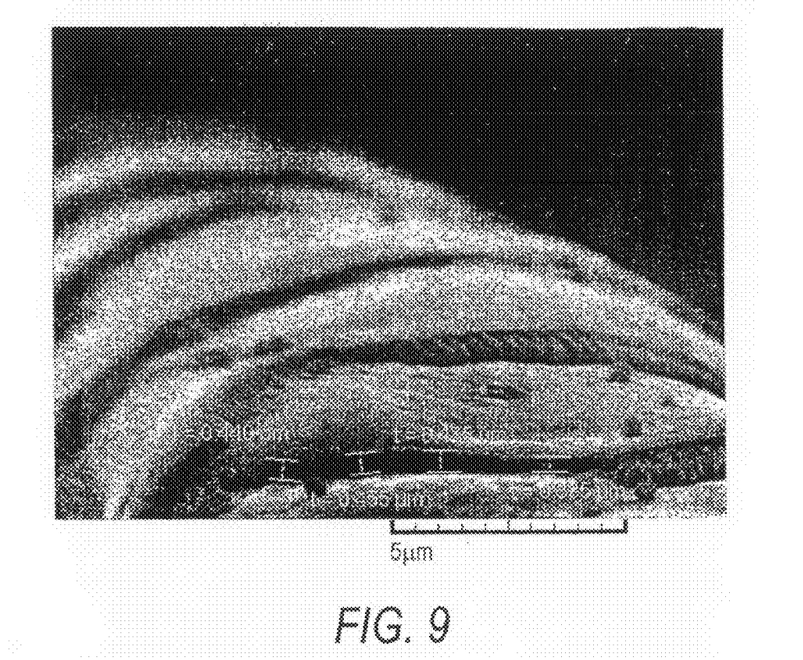
FIG. 9 is an SEM image of a cashmere fiber with an NIST internal standard at a magnification of 11,190× showing the lowest mean scale height.
Figure 10:
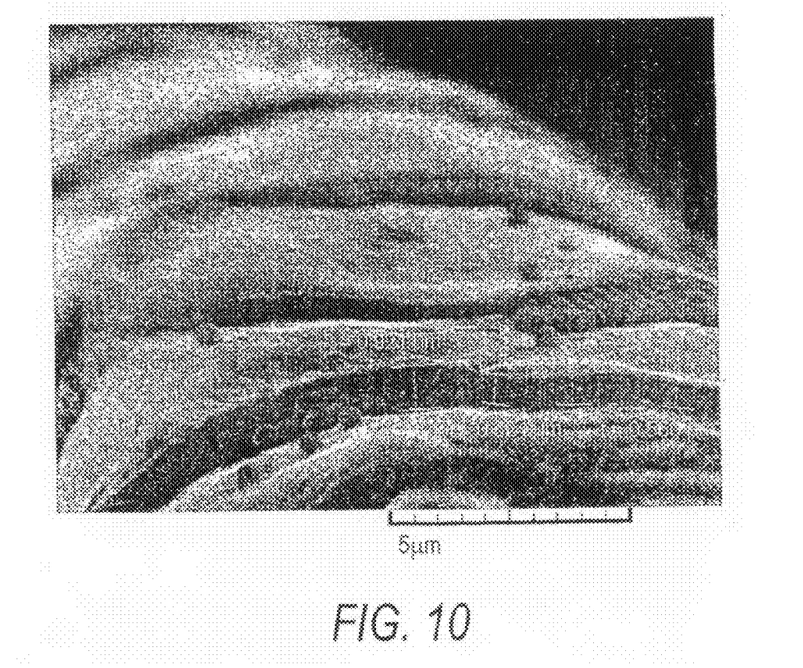
FIG. 10 is an SEM image of a cashmere fiber with an NIST standard at a magnification of 11,620× showing the highest mean scale height.

FIGS. 8-10 show the scale height of cashmere fibers with increasing magnification. The same is true of wool fibers in FIGS. 11-13 and alpaca fibers in FIGS. 14-16.

It is evident from an examination of the data from FIGS. 8-16, which is set forth in Table 1, below, that there is a much greater overlap in cuticle scale height (CSH) measurements for cashmere and wool fibers, as measured in accordance with the present invention, than would have been thought as a result of prior art studies employing the longitudinal measurement of such fibers.

Preparative Example

The Merino wool, E Tuo Ke cashmere and Alpaca samples were lab scoured according to the following industrial formulas and standard operating procedures using laboratory scale equipment:

Scouring Procedure

The cashmere, wool, and alpaca were scoured in a series of beakers with scouring water temperature between 40° C.-45° C.:

Beaker No. 1: Soaking with water, add soda ash ($Na_2CO_3$) adjusting the PH value adjusted to PH=8.

Beaker No. 2: Sodium tripolyphosphate 3/1000 solution Triton X-100 detergent 3/1000 solution pH value adjusted to be PH 6.5-7.5.

Beaker No. 3: Same as beaker No. 2.

Beaker No. 4: Water only (rinse)

Beaker No. 5: Same as the scouring beaker No. 4 water only (rinse)

The samples were then dyed using the following formula:

1. Dyeing formula

Pretreatment: Rinse in water at the temperature of 60° C. for 30 minutes Add Cibaflow CIR deaerator, 0.5 g/l.

Dyeing: Lanasol Blue 3 G 2.00% (owf) Ammonium sulfate ($(NH4)2SO4$): 4% Dye leveler: Albegal B: 2% Adjust the PH value adjusted to 5.4 with Acetic Acid. Liquor ratio: 1:100 Circulate 30 Minutes at 100° C.

After scouring and dyeing, all samples were air dried under ambient lab conditions and mounted on copper tape as previously described herein.

EXAMPLE

A sample size of 5 scales per fiber and two measurements (maximum and minimum height) per scale was employed.

In order to verify the calibration of the scanning electron microscope and confirm the veracity of the generated data an internal size standard in the form of Duke Scientific NIST Traceable Nanosphere Size Standards Lot Number 21270 with a mean diameter of 503±4 nm, standard deviation of 6.3 nm and coefficient of variation of 1.3% was introduced onto the surface of the fibers which were then sputter coated as previously detailed.

Figure 11:
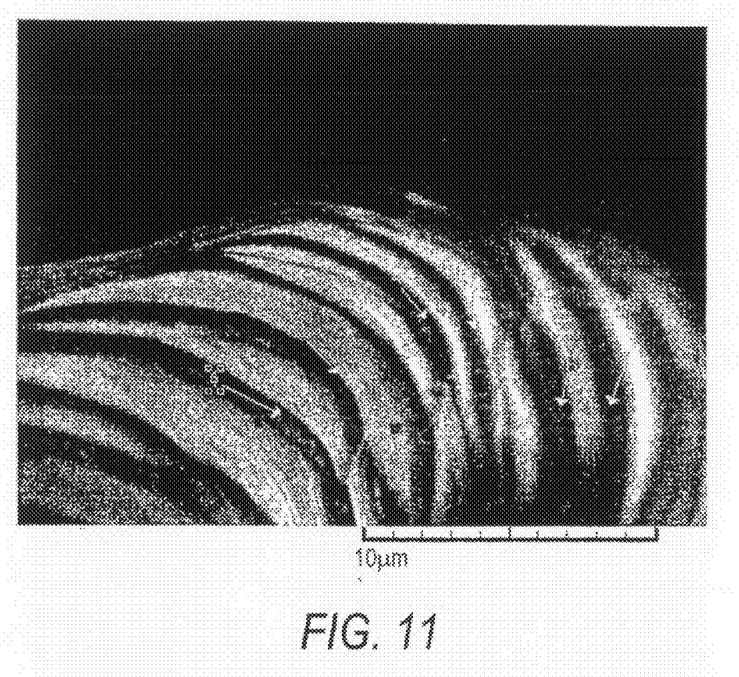
FIG. 11 is an SEM image of a wool fiber scale with an NIST internal standard and a scale sequence at a magnification of 6840×.
Figure 12:
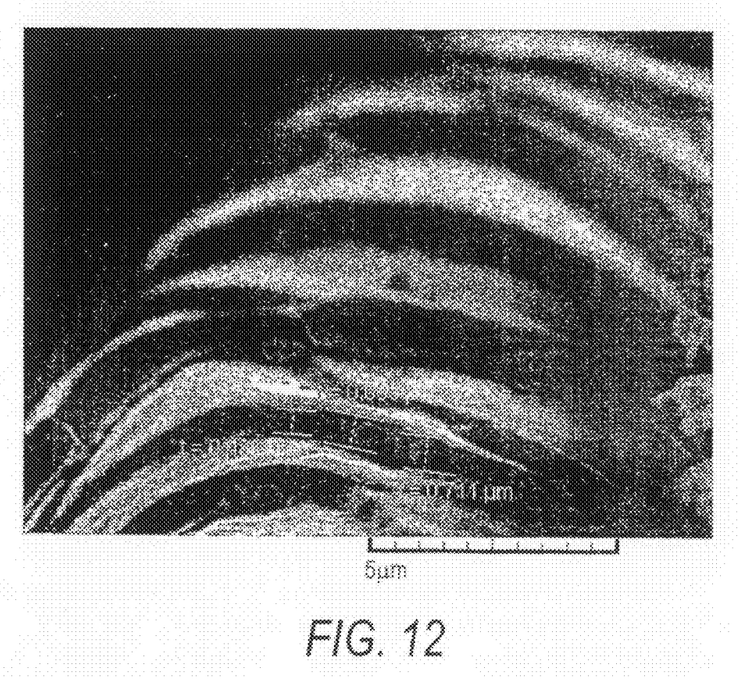
FIG. 12 is an SEM image of a wool fiber scale with an NIST internal standard at a magnification of 11,620× showing the lowest mean scale height.
Figure 13:
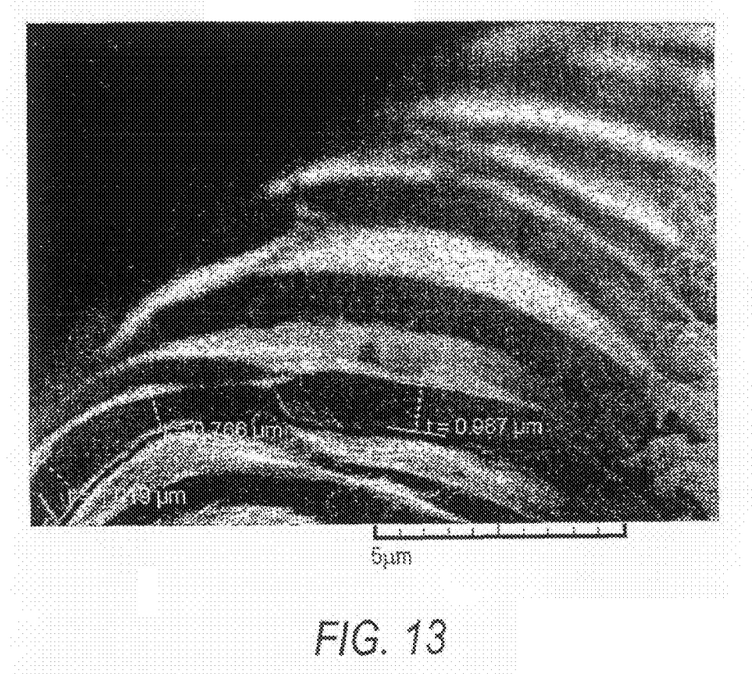
FIG. 13 is an SEM image of a wool fiber scale with an NIST internal standard at a magnification of 11,610× showing the highest mean scale height.
Figure 14:
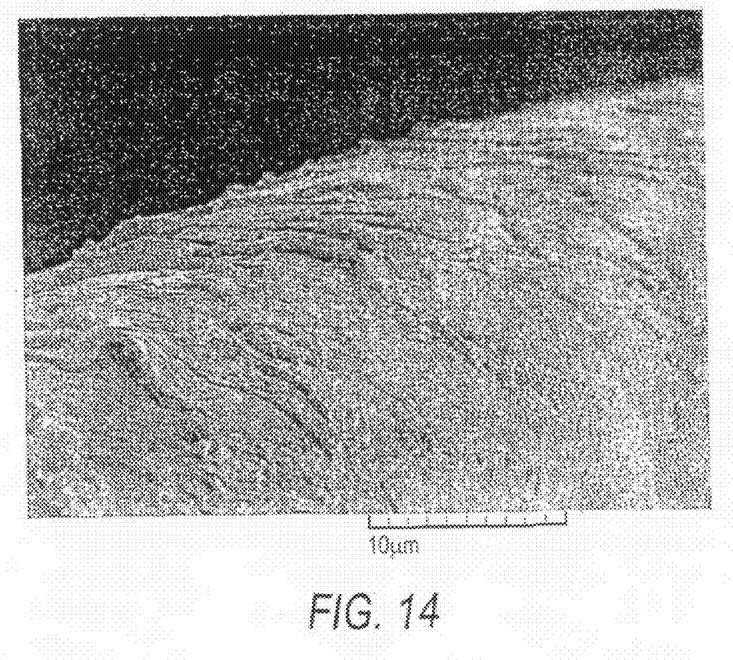
FIG. 14 is an SEM image of an alpaca fiber scale with an NIST internal standard and a scale sequence at a magnification of 6970×.
Figure 15:
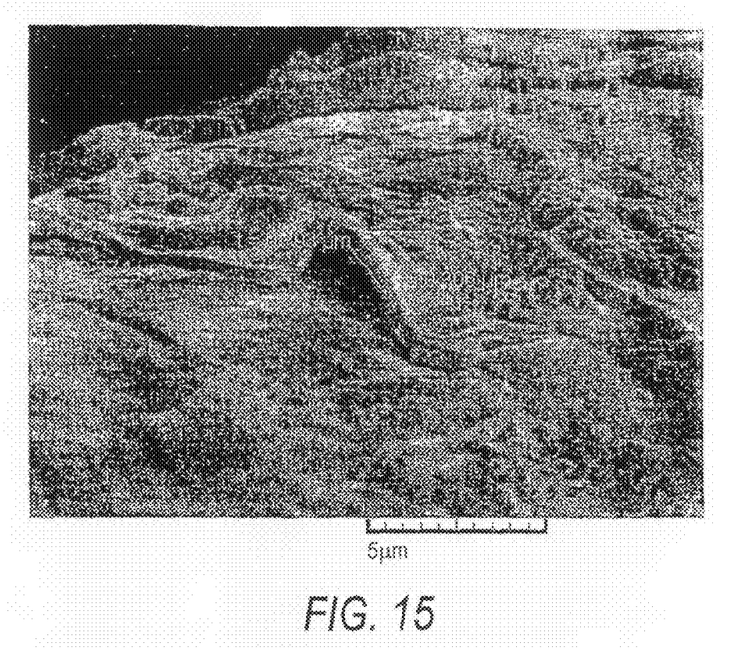
FIG. 15 is an SEM image of an alpaca fiber scale at a magnification of 8420× showing the highest mean scale height.
Figure 16:
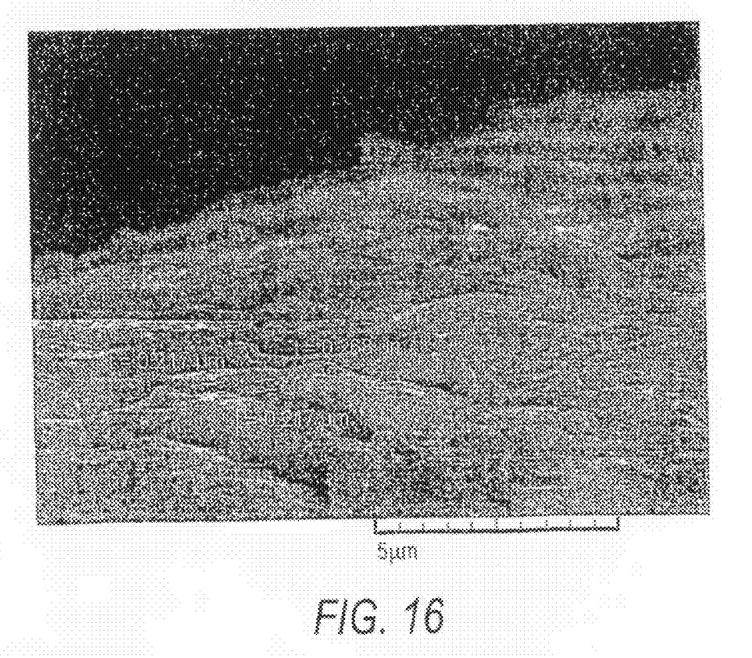
FIG. 16 is an SEM of an alpaca fiber scale at a magnification of 8420× showing the lowest mean scale height.

Sequential Scale Measurement of Vertically Oriented Specimens—Reactive Dyed Cashmere, Alpaca, and Merino Wool Fibers Table 1 below sets forth and FIGS. 8 to 16 depict the sequential vertically oriented scale height measurements taken from the dyed cashmere, wool and alpaca fibers samples previously described. FIGS. 8, 11, and 14 show the scales of each of the aforementioned fibers in sequence at relatively low magnification. FIGS. 9, 12, and 15 show the scale with the lowest mean scale height of the cashmere, wool and alpaca fibers which were measured, while FIGS. 10, 13, and 16 show the highest mean scale height.

TABLE 1

| Fiber Type | Source | Scale Height Grand Average & Standard Deviation | Mean Nanometers per scale | Minimum and Maximum Measurements Taken, Nanometers |
|---|---|---|---|---|
| Reactive Dyed Cashmere | 2 Year Old Doe E Tuo Ke Qi, Erdos Inner Mongolia (15 micron diameter). | Grand Avg. = 563 nm Std. Dev. = 123 nm | Scale 1: 510 nm Scale 2: 595 nm Scale 3: 569 nm Scale 4: 740 nm Scale 5: 405 nm | Scale 1 462 nm, 558 nm Scale 2 534 nm, 656 nm Scale 3 494 nm, 644 nm Scale 4 560 nm, 921 nm Scale 5 335 nm, 475 nm |
| Reactive Dyed Merino Wool | Catskill Merino (17 micron avg diameter approx) | Grand Avg. = 740 nm Std Dev. = 126 nm | Scale 1: 735 nm Scale 2: 637 nm Scale 3: 600 nm Scale 4: 893 nm Scale 5: 838 nm | Scale 1 627 nm, 842 nm Scale 2 635 nm, 639 nm Scale 3 489 nm, 711 nm Scale 4 766 nm, 1019 nm Scale 5 754 nm, 922 nm |
| Reactive Dyed Alpaca | Vartest Fiber Library | Grand Avg. = 254 nm Std Dev. = 192 nm | Scale 1: 358 nm Scale 2: 284 nm Scale 3: 348 nm Scale 4: 234 nm Scale 5: 211 nm | Scale 1: 306 nm, 393 nm Scale 2: 235 nm, 333 nm Scale 3: 338 nm, 355 nm Scale 4: 217 nm, 268 nm Scale 5: 221 nm, 201 nm |

Figure 17:
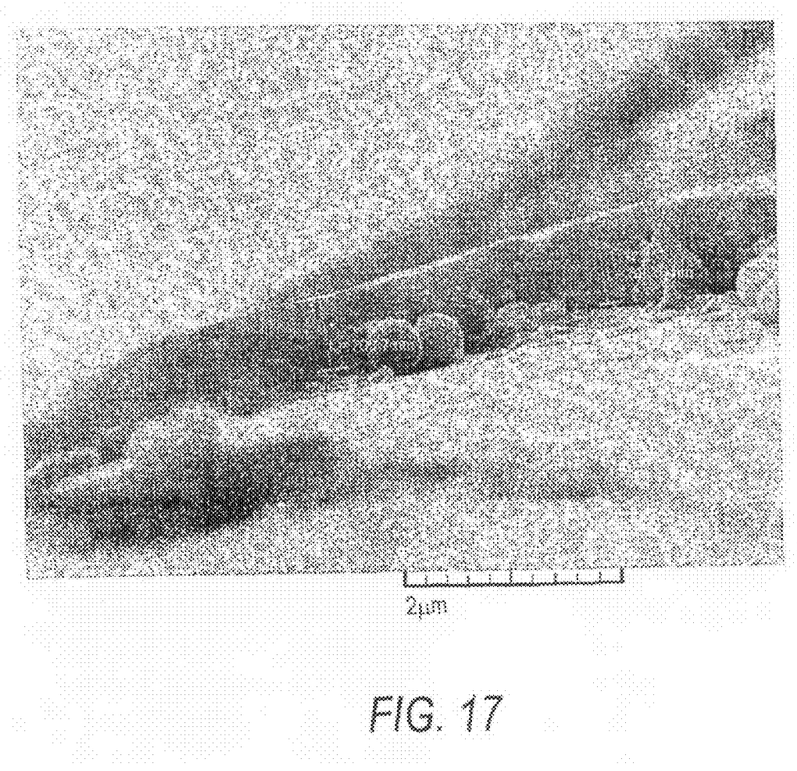
FIG. 17 is an SEM image of a white Chinese cashmere fiber with an NIST internal standard at a magnification of 40,229×.

Referring to FIG. 17, scales can be seen displaying thicknesses significantly greater than the statistical parameters observed by Kusch et al. [11] and Wortmann et al. [8]. The reactive dyed white Chinese cashmere of FIG. 17 is seen to have an average scale height of 746 nm, as measured in accordance with the method of the present invention.

Employing the prior art method of studying fibers, namely, measuring the fibers while extending longitudinally under an SEM, one investigator [11] found there was no overlap in cuticle scale height of wool fibers and specialty animal fibers, while a second investigator [8] found that cashmere samples had scale heights between 0.39±0.02 μm and 0.35±0.01 μm.

Contrary to the findings of the aforementioned investigators, by employing the method of the present invention scale heights of approximately twice the height previously reported have been found. Thus, the longitudinal measuring system of the prior art apparently caused cashmere fibers to be misidentified as wool. The method of the present invention represents a significant advance since it provides a more objective, accurate and precise manner of using the SEM for cuticle scale height analysis.

By using the vertical sequential scale height measurement method of the present invention, the textile scientist has been provided with the ability to obtain average scale height measurements which are more objective and accurate than were available heretofore.

REFERENCES

1. Metrology and the State: Revenue and Commerce, Ashworth, W. J., *Science, Vol.* 306, November 2004, pp. 1314-1317
2. Hamlyn, Paul F., Analysis of Animal Fibers, *Textiles Magazine*, Issue 3, 1998, pgs. 14-17
3. Animal Fiber Analysis Using Imaging Techniques—Part II: Addition of Scale Height Data. Robson D., Scottish Coll of Textiles—Galashiels) *Textile Research Journal* 70, No. 2: 116-121, (February 2000)
4. Zoccola et al., The Characterization of Cashmere., Tinctoria 96, No. 5: 40+, 6 pages (May 1999)
5. Marshall et al., Possible Identification of Specialty Fibers by Electrophoresis, *Textile Research Journal*, February 1984, pgs. 126-128
6. Sankaran, V. et al., Automated Fiber Identification and Analysis System, Proceedings of the 78$^{th}$ *World Congress of the Textile Institute*, May, 1997, pgs. 325-345
7. Langley, K. D. Practical Issues in Identifying Cashmere, *Second International Cashmere & Wool Determination Seminar*, Nov. 10 and 11, 2003 Erdos City, Inner Mongolia, pgs. 31-39
8. Wortmann and Arms, Qualitative Fiber Mixture Analysis by Scanning Electron Microscopy Parts 1-6, *Textile Research Journal*, July 1986, pp. 42.
9. IWTO Test Method 58-00 and Draft TM-58-97 Scanning Electron Microscopic Analysis of Specialty Fibers and Sheep's Wool and their Blends, International Wool Textile Organization
10. Dobb et al., Morphology of the Cuticle Layer in Wool Fibers and other Animal Fibers, *Journal of the Textile Institute*, Vol. 52, No. 4, April 1961, pp. 153-170
11. Kusch and Arms, Electron Scan Microscope Investigations to Distinguish Between Sheeps Wool and Goat Hair (e.g. Mohair), *Melliand Textilberichte (Eng. Edit)*, June 1983, pgs. 417-419

What is claimed is:

1. A method for objectively determining the cuticle scale height of a naturally-occurring, proteinaceous fiber, which comprises:
   a) selecting a naturally-occurring, proteinaceous fiber for cuticle scale height determination;
   b) mounting said fiber substantially vertically for imaging by a scanning electron microscope;
   c) imaging said fiber under said scanning electron microscope under sufficient magnification to discern the scale height of a vertically oriented cuticle; and
   d) taking at least one reading of the height of the cuticle along at least one scale of said fiber.

2. The method of claim 1, wherein a maximum and a minimum cuticle height reading is taken along at least one scale of said fiber.

3. The method of claim 2, wherein maximum and minimum readings of the cuticle height are taken along five (5) sequential scales.

4. The method of claim 1, wherein the naturally occurring fibers are selected from the group consisting of cashmere, wool, and alpaca.

* * * * *

UNITED STATES PATENT AND TRADEMARK OFFICE
CERTIFICATE OF CORRECTION

PATENT NO. : 7,833,568 B2  Page 1 of 1
APPLICATION NO. : 11/794655
DATED : November 16, 2010
INVENTOR(S) : Varley It is certified that error appears in the above-identified patent and that said Letters Patent is hereby corrected as shown below:

On the title page insert item (60),

-- Related U.S. Application Data (60) Provisional application No. 60/649,682, filed on
February 2, 2005 --

Signed and Sealed this
Twenty-first Day of June, 2011

David J. Kappos
*Director of the United States Patent and Trademark Office*